United States Patent
Park et al.

(10) Patent No.: US 9,758,801 B2
(45) Date of Patent: Sep. 12, 2017

(54) **MICROORGANISM OF *CORYNEBACTERIUM* SP. HAVING ENHANCED L-LYSINE PRODUCIBILITY AND METHOD FOR PRODUCING L-LYSINE USING SAME**

(71) Applicant: CJ CHEILJEDANG CORPORATION, Seoul (KR)

(72) Inventors: Sang Hee Park, Seoul (KR); Jun Ok Moon, Seoul (KR); Hyun Won Bae, Seoul (KR); Kwang Ho Lee, Seoul (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 0 days.

(21) Appl. No.: 15/032,279

(22) PCT Filed: Sep. 25, 2014

(86) PCT No.: PCT/KR2014/008932
§ 371 (c)(1),
(2) Date: Apr. 26, 2016

(87) PCT Pub. No.: WO2015/064917
PCT Pub. Date: May 7, 2015

(65) Prior Publication Data
US 2016/0251687 A1   Sep. 1, 2016

(30) Foreign Application Priority Data
Oct. 28, 2013  (KR) .................. 10-2013-0128634

(51) Int. Cl.
*C12N 1/20*   (2006.01)
*C12P 13/08*  (2006.01)

(52) U.S. Cl.
CPC ................ *C12P 13/08* (2013.01); *C12N 1/20* (2013.01)

(58) Field of Classification Search
USPC ...................................... 435/252.3
See application file for complete search history.

(56) References Cited

U.S. PATENT DOCUMENTS

| | | |
|---|---|---|
| 2010/0330624 A1 | 12/2010 | Jang et al. |
| 2013/0157370 A1 | 6/2013 | Jang et al. |
| 2014/0356518 A1 | 12/2014 | Park et al. |

FOREIGN PATENT DOCUMENTS

| | | |
|---|---|---|
| EP | 1792975 A1 | 6/2007 |
| EP | 1664318 B1 | 9/2009 |
| EP | 2107128 B1 | 10/2012 |
| JP | 2002191370 A | 7/2002 |
| KR | 1020090107665 | 10/2009 |
| KR | 1020130061570 | 6/2013 |
| RU | 2316588 C1 | 2/2008 |

OTHER PUBLICATIONS

C glutamicum protein fragment SEQ ID No. 4500, XP002769369, 2007, 1 page, Database Geneseq.
Extended European Search Report for Application No. 14858611.8 mailed on May 10, 2017, citing the above reference(s).
Japanese Office Action for Application No. 2016550437 dated Apr. 11, 2017, citing the above reference(s).
Georg Sindelar, et al., "Improving lysine production by Corynebacterium glutamicum through DNA microarray-based identification of novel target genes", Appl Microbiol Biotechnol, (2007), vol. 76, pp. 677-689.
International Search Report—PCT/KR2014/008932 dated Dec. 12, 2014.
Korean Notice of Allowance—KR Application 10-2013-0128634 dated Feb. 9, 2015, citing enumerated references listed within.
Transposase [Corynebacterium glutamicum ATCC 13032], Posted May 23, 2013, pp. 1-3, Retrieved from the Internet Apr. 22, 2014, <URL:http://www.ncbi.nlm.nih.gov/protein/62389788?report=genbank&log$=prottop&blast_rank=2&RID=NBW37X9201R>.
Written Opinion—PCT/KR2014/008932 dated Dec. 12, 2014.
Russian Office Action for Application No. 2016114418/10 dated Jun. 21, 2017, citing the above reference(s).
Russian Search Report for Application No. 2016114418/10 dated Jun. 19, 2017, citing the above reference(s).
UNIPROTKB Q8NL10, Jan. 10, 2002, retrieved from the Internet on Jun. 16, 2017: www.uniprot.org/uniprot/Q8NL10.

*Primary Examiner* — Tekchand Saidha
(74) *Attorney, Agent, or Firm* — Cantor Colburn LLP

(57) ABSTRACT

Provided are a microorganism of *Corynebacterium* sp., which is modified to over-express a NCgl0862 gene of *Corynebacterium glutamicum*, so as to have enhanced L-lysine producibility, and a method of producing L-lysine by using the microorganism.

4 Claims, No Drawings

MICROORGANISM OF *CORYNEBACTERIUM* SP. HAVING ENHANCED L-LYSINE PRODUCIBILITY AND METHOD FOR PRODUCING L-LYSINE USING SAME

TECHNICAL FIELD

The present invention relates to a microorganism belonging to the genus *Corynebacterium* having enhanced L-lysine producibility and a method of producing L-lysine by using the microorganism.

BACKGROUND ART

L-lysine is a type of an essential amino acid, and is used in the fields of feed, medicine and food. L-lysine is mainly produced by direct fermentation using a microorganism such as *Escherichia coli* or *Corynebacterium*, and in this regard, improvements of L-lysine producibility by developments in production strains having improved yields or improvements in fermentation processes may result in significant economic effects.

In regard to a method of improving the production efficiency of lysine, a method of amplifying a gene involved in a biosynthetic pathway of lysine or modifying a promoter of the gene to increase the activity of enzymes involved in a biosynthetic pathway of lysine has been used. In addition, research into genes, other than genes involved in a biosynthetic pathway of lysine, has been continuously conducted to increase the producibility of lysine.

The inventors of the present invention attempted to prepare and explore a wild-type DNA library of *Corynebacterium glutamicum* to screen traits related to the producibility of lysine. Consequently, with the enhanced expression of NCgl0862 gene, lysine was confirmed to be produced efficiently, thereby completing the present invention. Until now, studies of microorganisms belonging to the genus *Corynebacterium* capable of producing L-lysine by additionally introducing *Corynebacterium*-derived NCgl0862 gene thereto have not yet been reported.

DETAILED DESCRIPTION OF THE INVENTION

Technical Problem

The present invention provides a microorganism belonging to the genus *Corynebacterium* in which expression of a polynucleotide encoding an amino acid sequence of SEQ ID NO: 1 is enhanced.

The present invention provides a method of producing L-lysine by using the microorganism.

Technical Solution

An aspect of the present invention provides a microorganism belonging to the genus *Corynebacterium* in which expression of a polynucleotide encoding an amino acid sequence of SEQ ID NO: 1 is enhanced.

The polynucleotide may encode an amino acid sequence having about 70% or higher, about 75% or higher, about 80% or higher, about 85% or higher, about 90% or higher, about 92% or higher, about 95% or higher, about 97% or higher, about 98% or higher, or about 99% or higher sequence homology with the amino acid sequence of SEQ ID NO: 1. The term "homology," as used herein, refers to percent identity between two polynucleotides or two polypeptide moieties. A sequence homology between one moiety and another moiety can be determined by using methods known in the art. For example, such a sequence homology may be determined by a BLAST algorithm as disclosed in literature [refer to Karlin and Altschul, Pro. Natl. Acad. Sci. USA, 90, 5873 (published in 1993)] or by Pearson's FASTA algorithm [refer to Methods Enzymol., 183, 63 (published in 1990)]. Based on the BLAST algorithm, programs called BLASTN or BLASTX are also developed [refer to www.ncbi.nlm.nih.gov].

The expression of the polynucleotide may be enhanced by a modification of an expression regulatory sequence by substitution or mutation, a mutation introduced to the polynucleotide sequence, a change in an initiation codon, an increase in copy number of the polynucleotide by introduction through chromosomal insertion or a vector, or combinations thereof.

The expression regulatory sequence of the polynucleotide may be modified. The expression regulatory sequence controls expression of a polynucleotide operably linked thereto, and for example, may include a promoter, a terminator, an enhancer, a silencer, and a Shine-Dalgarno sequence. The polynucleotide may have a change in an initiation codon. The initiation codon consisting of TTG or GTG may be substituted with ATG so that the enzymatic activity of a corresponding gene may be increased. The polynucleotide may be inserted into a particular site of chromosomes to thereby increase the copy number. Here, the particular site may include, for example, a transposon site or an intergenic site. In addition, the polynucleotide may be inserted into an expression vector, which is introduced to a host cell, to thereby increase the copy number.

The polynucleotide may include, for example, a nucleotide sequence of SEQ ID NO: 2.

The term "operably linked," as used herein, refers to a functional linkage between the regulatory sequence and the polynucleotide sequence, whereby the regulatory sequence controls transcription and/or translation of the polynucleotide sequence. The regulatory sequence may be a strong promoter that can increase an expression level of the polynucleotide. The regulatory sequence may be a promoter derived from a microorganism belonging to the genus *Corynebacterium* or may be a promoter derived from other microorganisms. The promoter may be, for example, a trc promoter, a gap promoter, a tac promoter, a T7 promoter, a lac promoter, a trp promoter, an araBAD promoter, or a cj7 promoter. The regulatory sequence may be modified so that, for example, a promoter sequence of a major gene involved in a biosynthesis pathway of lysine exhibits more enhanced promoter activity in a microorganism belonging to the genus *Corynebacterium*. The regulatory sequence may be, for example, a lysCP1 promoter. The term "lysCP1 promoter," as used herein, refers to a strong promoter of which the enzymatic activity is improved approximately 5 times greater than that of a wild-type by increasing expression level of a gene encoding aspartate kinase gene, wherein the expression level is increased by substituting sequences at a promoter site of genes each encoding aspartate kinase and aspartate semialdehyde dehydrogenase (Korean Patent No. 10-0930203).

The term "vector," as used herein refers to a polynucleotide construct containing a regulatory sequence of a gene and a sequence of a gene and configured to express a target gene in a suitable host cell. Alternatively, the vector may also refer to a polynucleotide construct containing sequences available for homologous recombination, so that due to the vector introduced to a host cell, a regulatory sequence of an endogenous gene in a genome of the host cell may be changed, or a target gene that can be expressed may be inserted into a particular site of a genome of the host. In this regard, the vector used in the present invention may further include a selection marker to determine introduction of the vector to the host cell or insertion of the vector to a chromosome of the host cell. The selection marker may include a marker conferring a selectable phenotype, such as drug resistance, auxotrophy, resistance against a cytotoxic agent, or expression of a surface protein. In the environment treated with such a selection agent, since only cells expressing the selection marker can survive or show different phenotypic traits, transformed cells may be selected.

The vector used in the present invention may be, for example, a vector pECCG122 that can self-replicate in both directions in *E. coli* and *Coryne*-type bacteria (Korean Patent No. 10-0057684), or a vector pDZ used to transform a host cell to allow insertion of a gene encoding a target protein into chromosomes of the host cell, wherein and the vector pDZ is not replicable in *Corynebacterium glutamicum* (Korean Patent No. 10-0924065). In addition, the vector used herein may be, for example, a vector pDZTn derived from the vector pDZ and available for insertion of a gene into a transposon site on chromosome of *Corynebacterium glutamicum* ATCC13032 strains (Korean Patent No. 10-1126041), but the vector is not limited thereto.

The term "transformation," as used herein, refers to introducing a polynucleotide to a host cell so that the polynucleotide may be replicable as an extragenomic element or as being inserted into a genome of the host cell. A method of transforming the vector used in the present invention may include a method of introducing a nucleic acid to a cell. In addition, as disclosed in the related art, an electric pulse method may be carried out depending on a host cell.

The microorganism belonging to the genus *Corynebacterium* may be, for example, *Corynebacterium glutamicum*, *Corynebacterium efficiens*, *Corynebacterium diphtheriae*, or *Corynebacterium ammoniagenes*.

The microorganism belonging to the genus *Corynebacterium* may have L-lysine producibility. The microorganism may have improved L-lysine producibility by introducing the above-described polynucleotide to the microorganism belonging to the genus *Corynebacterium* and having L-lysine producibility.

The term "having L-lysine producibility," as used herein, refers to having the ability to produce and secrete L-lysine in a culture medium when culturing the microorganism therein. The microorganism may be capable of producing and accumulating L-lysine in the culture medium in larger quantities compared to a wild-type or parent strain.

The microorganism belonging to the genus *Corynebacterium* and having L-lysine producibility may have enhanced or reduced expression of a gene related to the NADPH production and/or a gene related to the L-lysine biosynthesis or secretion, or may have a gene substituted with a foreign gene. The gene related to the NADPH production may include, for example, a gene encoding glucose dehydrogenase, a gene encoding gluconate kinase, a gene encoding glyceraldehyde-3-phosphate dehydrogenase, a gene encoding glucose 6-phosphate dehydrogenase, or a gene encoding 6-phosphogluconate dehydrogenase. The gene related to the L-lysine biosynthesis may include, for example, a gene encoding aspartate aminotransferase, a gene encoding aspartate kinase, a gene encoding aspartate semialdehyde dehydrogenase, a gene encoding dehydrodipicolinate synthase, a gene encoding dehydrodipicolinate reductase, a gene encoding dehydrodipicolinate reductase, a gene encoding meso-diaminopimelate dehydrogenase, or a gene encoding diaminodipimelate decarboxylase. The gene related to the L-lysine secretion may include lysE, which is a lysine export carrier gene. The microorganism belonging to the genus *Corynebacterium* and having L-lysine producibility may also obtain such L-lysine producibility by using xylose as a carbon source.

In an embodiment, the microorganism belonging to the genus *Corynebacterium* may be *Corynebacterium glutamicum* KCCM11016P (KFCC10881) (Korean Patent No. 10-0159812).

In another embodiment, into the microorganism belonging to the genus *Corynebacterium*, a polynucleotide encoding aspartate aminotransferase, a polynucleotide encoding aspartate kinase, a polynucleotide encoding aspartate semialdehyde dehydrogenase, a polynucleotide encoding dehydrodipicolinate synthase, a polynucleotide encoding dehydrodipicolinate reductase, and a polynucleotide encoding diaminodipimelate decarboxylase may be introduced. For example, the microorganism belonging to the genus *Corynebacterium* may be *Corynebacterium glutamicum* KCCM10770P (Korean Patent No. 10-0924065).

In another embodiment, the microorganism belonging to the genus *Corynebacterium* may be *Corynebacterium glutamicum* KCCM11347P (KFCC10750).

In another embodiment, the microorganism belonging to the genus *Corynebacterium* may obtain lysine producibility by introducing a mutant of a polynucleotide encoding pyruvate carboxylase (pyc), a mutant of a polynucleotide encoding homoserine dehydrogenase (hom), and a mutant of a polynucleotide encoding aspartate kinase (lysC) (Binder et al, Genome Biology, 2012, 13:R40). The microorganism may be, for example, *Corynebacterium glutamicum* CJ3P.

Another aspect of the present invention provides a method of producing L-lysine, the method comprising: culturing the microorganism; and obtaining L-lysine from the culture.

The microorganism is the same as described above.

The culturing of the microorganism may be performed in an appropriate medium under culture conditions that are known in the art. Such a culturing process may be easily adjusted depending on a microorganism to be selected. The culturing method may include one or more selected from the group consisting of batch culture, continuous culture, and fed-batch culture.

The medium used in the culturing may meet the requirements of a particular microorganism. The medium may be selected from the group consisting of carbon sources, nitrogen sources, trace elements, and combinations thereof.

The carbon source may be selected from the group consisting of carbohydrates, lipids, fatty acids, alcohols, organic acids, and combinations thereof. The carbohydrate may be glucose, sucrose, lactose, fructose, maltose, starch, cellulose, or a combination thereof. The lipid may be soybean oil, sunflower oil, castor oil, coconut oil, or a combination thereof. The fatty acid may be palmitic acid, stearic acid, linoleic acid, or a combination thereof. The alcohol may be glycerol or ethanol. The organic acid may be acetic acid.

The nitrogen source may include an organic nitrogen source, an inorganic nitrogen source, or a combination thereof. The organic nitrogen source may be selected from the group consisting of peptone, yeast extract, meat extract, malt extract, corn steep liquid (CSL), soybean meal, and combinations thereof. The inorganic nitrogen source may be selected from the group consisting of urea, ammonium sulfate, ammonium chloride, ammonium phosphate, ammonium carbonate, ammonium nitrate, and combinations thereof.

The medium may include one selected from the group consisting of phosphorous, metal salts, amino acids, vitamins, precursors, and combinations thereof. The phosphorous source may include potassium dihydrogen phosphate, dipotassium phosphate, a sodium-containing salt corresponding thereto. The metal salt may be magnesium sulfate and iron sulfate.

The medium or individual components thereof may be added to the culture medium in a batch mode, a continuous mode, or a fed-batch mode.

In the culturing method, the pH of the culture may be adjusted. The pH adjustment may be performed by adding ammonium hydroxide, potassium hydroxide, ammonia, phosphoric acid, or sulfuric acid to the culture. Further, the culturing method may include prevention of air bubble generation. The prevention of air bubble generation may be performed by using an antifoaming agent. The antifoaming agent may include fatty acid polyglycol ester. Further, the culturing method may include injection of gas into the culture. The gas may include any gas capable of maintaining the aerobic condition of the culture. The gas may be oxygen or oxygen-containing gas. The oxygen-containing gas may include air. In the culturing, the temperature of the culture may be 20 to 45° C., for example, 22 to 42° C., or 25 to 40° C. The culturing may be continued until the production of L-lysine reaches a desired level.

The produced L-lysine may be, for example, recovered from the culture by treating the culture with sulfuric acid or hydrochloric acid, followed by performing a combination of processes such as anion exchange chromatography, concentration, crystallization, and isoelectric point precipitation.

Advantageous Effects of the Invention

The producibility of L-lysine may be increased by using a microorganism according to an aspect of the present invention.

The producibility of L-lysine may be increased by using a method of producing L-lysine according to another aspect of the present invention.

MODE OF THE INVENTION

Hereinafter, the present application will be described in more detail with reference to Examples. However, these Examples are for illustrative purposes only, and the scope of the present application is not intended to be limited by these Examples.

EXAMPLE 1

Preparation of Wild-Type *Corynebacterium glutamicum* Genomic DNA Library

The genomic DNA of *Corynebacterium glutamicum* ATCC13032 strain was prepared, and then, treated with a restriction enzyme Sau3AI, so as to obtain partial fragments of 6 to 8 kb. The fragment was ligated to a shuttle vector pECCG122 for transformations of *E. coli* and *Corynebacterium*, the shuttle vector including ends for a restriction enzyme BamHI. Then, *E. coli* DH5α was transformed with the resulting vector and spread on LB solid medium containing kanamycin (25 mg/L). Colonies transformed with the vector into which the fragments were inserted were selected by PCR (using primers of SEQ ID NOs: 3 and 4) and subjected to a mixed culture, and plasmids were obtained therefrom by a generally known plasmid extraction method.

SEQ ID NO: 3:
TCAGGGTGTAGCGGTTCGGTTTAT.

SEQ ID NO: 4:
CCGCGCGTAATACGACTCACTATA.

EXAMPLE 2

Introduction of Library and Selection of Strain Having Improved Lysine Producibility

*Corynebacterium glutamicum* KCCM11016P strain, which produces lysine, was transformed with the recombinant vector prepared in Example 1 using an electric pulse method, and then, was spread on a complex medium plate described below.
<Complex Medium Plate>

20 g of glucose, 50 g of $(NH_4)_2SO_4$, 10 g of peptone, 5 g of yeast extract, 1.5 g of urea, 5 g of $KH_2PO_4$, 10 g of $K_2HPO_4$, 0.5 g of $MgSO_4.7H_2O$, 100 μg of biotin, 1,000 μg of thiamine HCl, 2,000 μg of calcium-pantothenate, 2,000 μg of nicotinamide, 20 g of agar, and 25 mg of kanamycin (based on 1 L of distilled water).

About 2,000 colonies were inoculated into each well of a 96 deep-well plate (manufactured by Bioneer Company) containing 200 uL of a complex liquid medium described below, and then, cultured by shaking at 200 rpm and 30□ for 24 hours. According to a lysine oxidase method, 50 ul of the each culture was added to a 96 well plate on which a lysine oxidase-containing reaction mixture (containing 200 ul of potassium phosphate (pH 7.5), 0.04 ul of lysine oxidase (0.1 unit/ul), 0.04 ul of peroxidase (1 unit/ul), and 0.4 mg of ABTS) was dispensed. After a reaction for 30 minutes, the absorbance at $OD_{405nm}$ was measured and the degree of color formation was compared. Among them, 7 types of experimental groups, each having higher absorbance than a control group (KCCM11016P/pECCG122), were selected.
<Complex Liquid Medium>

20 g of glucose, 10 g of peptone, 5 g of yeast extract, 1.5 g of urea, 4 g of $KH_2PO_4$, 8 g of $K_2HPO_4$, 0.5 g of $MgSO_4.7H_2O$, 100 μg of biotin, 1,000 μg of thiamine HCl, 2,000 μg of calcium-pantothenate, and 2,000 μg of nicotinamide (based on 1 L of distilled water).

The individual strains were inoculated into 250 ml corner-baffled flask containing 25 ml of a seed medium described below, and then, cultured by shaking at 200 rpm and 30□ for 20 hours. Then, 1 ml of the seed culture was inoculated into 250 ml corner-baffled flask containing 24 ml of a production medium described below, and then, cultured by shaking at 200 rpm and 37□ for 96 hours. After completing the culturing, L-lysine concentrations were analyzed by HPLC, and the analysis results are shown in Table 1.
<Seed Medium (pH 7.0)>

20 g of glucose, 10 g of $(NH_4)_2SO_4$, 10 g of peptone, 5 g of yeast extract, 1.5 g of urea, 4 g of $KH_2PO_4$, 8 g of $K_2HPO_4$, 0.5 g of $MgSO_4.7H_2O$, 100 μg of biotin, 1,000 μg of thiamine HCl, 2,000 μg of calcium pantothenate, and 2,000 μg of nicotinamide (based on 1 L of distilled water).
<Production Medium (pH 7.0)>

100 g of glucose, 40 g of $(NH_4)_2SO_4$, 2.5 g of soybean protein, 5 g of corn steep solid, 3 g of urea, 1 g of $KH_2PO_4$, 0.5 g of MgSO$_4$.7H$_2$O, 100 μg of biotin, 1,000 μg of thiamine HCl, 2,000 μg of calcium pantothenate, 3,000 μg of nicotinamide, and 30 g of CaCO$_3$ (based on 1 L of distilled water).

TABLE 1

| Strain number | | Lysine concentration (g/L) | Average (g/L) |
|---|---|---|---|
| KCCM11016P/pECCG122 | 1 | 43.1 | 43.4 |
| | 2 | 42.5 | |
| | 3 | 44.5 | |
| KCCM11016P/M2 | 1 | 46.5 | 47.6 |
| | 2 | 47.5 | |
| | 3 | 48.7 | |
| KCCM11016P/L52 | 1 | 48.8 | 48.1 |
| | 2 | 47.9 | |
| | 3 | 47.5 | |
| KCCM11016P/B20 | 1 | 42.5 | 43.2 |
| | 2 | 43.5 | |
| | 3 | 43.5 | |
| KCCM11016P/B1 | 1 | 44.1 | 44.1 |
| | 2 | 44.2 | |
| | 3 | 43.9 | |
| KCCM11016P/A59 | 1 | 42.8 | 43.4 |
| | 2 | 43.8 | |
| | 3 | 43.7 | |
| KCCM11016P/A9 | 1 | 43.5 | 44.0 |
| | 2 | 44.5 | |
| | 3 | 43.9 | |
| KCCM11016P/D50 | 1 | 42.9 | 43.2 |
| | 2 | 43.9 | |
| | 3 | 42.9 | |

Based on the results above, KCCM11016P/M2 and KCCM11016P/L52 showing increased lysine producibility compared to that of the control group were selected, and then, plasmids were extracted therefrom, followed by sequencing analysis using primers of SEQ ID NOs: 3 and 4. The plasmid derived from KCCM11016P/M2 was named pEC-L1, and the plasmid derived from KCCM11016P/L52 was named pEC-L2. The pEC-L1 plasmid includes from about 200 base pairs (bp) upstream of an open reading frame (ORF) initiation codon of NCgl0857 gene to about 200 bp downstream of an ORF stop codon of NCgl0862 gene. The pEC-L2 plasmid includes from about 250 bp downstream of an ORF stop codon of NCgl0861 gene to about 300 bp upstream from an ORF initiation codon of NCgl0865 gene. Accordingly, it was confirmed that the two types of plasmids both include NCgl0862 gene in common.

EXAMPLE 3

Preparation of Vector for Replacing Promoter of NCgl0862 Gene

Based on the results obtained in Example 2, to confirm whether over-expression of the NCgl0862 gene practically induces the improvement of lysine producibility, a vector configured to replace a promoter of the NCgl0862 gene on chromosome was prepared. For the replacement of the promoter, a wild-type promoter (lysCP) and a modified promoter lysCP1 were used as promoters of lysC gene.

A detailed description is provided as follows.

Based on the GenBank of the National Institutes of Health (NIH GenBank, US), pairs of primers (SEQ ID NOs: 5 and 6 or SEQ ID Nos: 7 and 8) to be configured to respectively amplify the upstream and downstream of the ORF initiation codon of the NCgl0862 gene (SEQ ID NO: 2) were designed. In addition, a pair of primers (primers of SEQ ID NOs: 9 and 10) was designed to amplify a promoter site from sequences upstream of the lysC gene. SEQ ID No. and sequences of the primers are shown below. Underlined sequences indicate sites recognized by restriction enzymes.

SEQ ID NO: 5 is    GT<u>GAATTC</u>CGCCCGTATGGTGATT

SEQ ID NO: 6:     TA<u>GGATCC</u>AGAAGGCGCTGGCTT

SEQ ID NO: 7:     AG<u>GGATCC</u>TAA<u>CATATG</u>GAAGCCGAAGCACCT

SEQ ID NO: 8:     AG<u>GTCGAC</u>TCATTCGTTCATAATT

SEQ ID NO: 9:     TA<u>GGATCC</u>TAGGGAGCCATCTTTTGGGG

SEQ ID NO: 10:    TAA<u>CATATG</u>TGTGCACCTTTCGATCTACG

PCR was performed by using the genomic DNA of Corynebacterium glutamicum KCCM11016P strain as a template and pairs of primers of SEQ ID NOs: 5 and 6 and SEQ ID NOs: 7 and 8, and SEQ ID NOs: 9 and 10 thereby obtaining 300 by DNA fragments each having left and right flanking sequences of the ORF initiation codon of the NCgl0862 gene and a fragment of a wild-type promoter of the lysC gene, hereinafter referred to as "lysCP promoter". Conditions for the PCR amplification include denaturation at 94☐ for 5 minutes, 30 cycles of denaturation at 94☐ for 30 seconds, annealing at 56☐ for 30 seconds, and polymerization at 72☐ for 30 seconds, and then polymerization at 72☐ for 7 minutes. Each of the 300 bp product amplified by PCR having left or right flanking sequence of the ORF initiation codon of the NCgl0862 gene was respectively treated with EcoRI and BamHI, and BamHI and SalI, and then, ligated to a DNA fragment obtained by treating a vector pDZ for chromosomal insertion of a microorganism belonging to the genus Corynebacterium with restriction enzymes, SalI and EcoRI, thereby obtaining a vector.

To amplify the lysCP promoter or the lysCP1 promoter, PCR was performed by using the genomic DNA of Corynebacterium glutamicum ATCC 13032 strain or KCCM11016P-lysCP1 strain (Korean Patent No. 10-0930203) as a template and a pair of primers of SEQ ID NOs: 9 and 10, thereby obtaining 300 bp fragments of the lysCP promoter and the lysCP1 promoter. DNA fragments of the lysC wild-type promoter and the lysCP1 promoter were treated with BamHI and NdeI. Then, the vector obtained above was ligated to the DNA fragment obtained by treatment with BamHI and NdeI, thereby preparing recombinant plasmids pDZ-lysCP_N0862 and pDZ-lysCP1_N0862.

EXAMPLE 4

Analysis of Lysine Producibility of Strain with Replaced Promoter of NC210862 Derived Lysine-droducing Strain The recombinant plasmids pDZ-lysCP_N0862 and pDZ-lysCP1_N0862 prepared in Example 3 were transformed into Corynebacterium glutamicum KCCM11016P according to an electric pulse method (Van der Rest et al., Appl Microbiol Biotechnol 52:541-545, 1999). According to a generally known chromosomal homologous recombination, strains in which the lysC promoter was inserted into a promoter site of the NCgl0862 gene were selected by PCR (primers of SEQ ID NOs: 5 and 8). The selected recombinant strains were named Corynebacterium glutamicum KCCM11016P::lysCP_N0862 and KCCM11016P::lysCP1_N0862.

To identify lysine producibility of such prepared lysine-producing strains, KCCM11016P::lysCP_N0862 and KCCM11016P::lysCP1_N0862, the strains were seed- and production-cultured in the same manner as in Example 2, and then, lysine concentrations in each culture were analyzed as shown below (see Table 2).

TABLE 2

| Strain number | | 1st Lysine concentration (g/L) | 1st Average (g/L) | 2nd Lysine concentration (g/L) | 2nd Average (g/L) | 3rd Lysine concentration (g/L) | 3rd Average (g/L) |
|---|---|---|---|---|---|---|---|
| KCCM11016P | 1 | 42.0 | 42.1 | 43.1 | 42.4 | 41.9 | 42.1 |
| | 2 | 42.3 | | 41.9 | | 42.2 | |
| | 3 | 42.1 | | 42.1 | | 42.1 | |
| KCCM11016P::lysCP_N0862 | 1 | 42.8 | 42.6 | 42.9 | 43.0 | 42.0 | 42.5 |
| | 2 | 42.6 | | 43.4 | | 42.5 | |
| | 3 | 42.5 | | 42.7 | | 43.1 | |
| KCCM11016P::lysCP1_N0862 | 1 | 44.1 | 44.0 | 45.1 | 44.7 | 44.1 | 43.9 |
| | 2 | 44.1 | | 44.1 | | 43.9 | |
| | 3 | 43.9 | | 44.9 | | 43.8 | |

As shown in Table 2, it was confirmed that lysine producibility of the KCCM11016P::lysCP_N0862 strain in which the promoter was replaced with the lysC wild-type promoter was increased 1% by average compared to that of the parent strain, KCCM11016P, and that lysine producibility of the KCCM11016P::lysCP1_N0862 strain in which the promoter was replaced with the lysCP1 promoter was increased 4% by average compared to that of the parent strain. Afterwards, the KCCM11016P::lysCP1_N0862 strain was named CA01-2269 and deposited at the Korean Culture Center of Microorganisms (KCCM) on Jun. 12, 2013 with Accession No. KCCM11430P.

EXAMPLE 5

Preparation of Vector for Additional Chromosomal Insertion of NCgl0862 Gene

To allow insertion of a desired gene into a position of a transposon gene, pDZTN vector designed from pDZ vector was used as a basic vector, thereby designing and preparing a vector configured to additionally insert the NCgl0862 gene of Example 2 into chromosomes.

Based on the reported sequences, primers (SEQ ID NOs: 7 and 12) were synthesized to amplify sites of the NCgl0862 gene. PCR was performed by using the chromosomes of Corynebacterium glutamicum ATCC 13032 as a template, thereby amplifying an about 370 bp ORF site of the NCgl0862 gene.

In addition, primers (SEQ ID NOs: 10 and 11) were synthesized to amplify sites of a promoter of the lysC gene. PCR was performed by using the chromosomes of Corynebacterium glutamicum KCCM11016P-lysCP1 introduction strain as a template, thereby amplifying an about 300 bp promoter site. Here, conditions for the PCR amplification include denaturation at 94☐ for 5 minutes, 30 cycles of denaturation at 94☐ for 30 seconds, annealing at 56☐ for 30 seconds, and polymerization at 72☐ for 30 seconds, and then polymerization at 72☐ for 7 minutes.

SEQ ID NO: 11: TAACTAGTTAGGGAGCCATCTTTTGGGG

Gene fragments amplified by PCR were treated with restriction enzymes SpeI and NdeI to thereby obtain DNA fragments thereof. The DNA fragments were ligated to the vector pDZTN for chromosomal insertion having ends of a restriction enzyme SpeI. Then, E. coli DH5α was transformed with the resulting vector and spread on LB solid medium containing 25 mg/L of kanamycin. Colonies transformed with the vector including a desired gene inserted thereinto were selected by PCR (primers of SEQ ID NOs: 12 and 13), and plasmids were obtained by performing a generally known plasmid extraction method, and then, named pDZTN-N0862.

SEQ ID NO: 12: TAACTAGTATGCTCGGTCCGGGCA

SEQ ID NO: 13: GCAGGCGGTGAGCTTGTCAC

EXAMPLE 6

Analysis of Lysine Producibility of Strain Including NCgl0862 Additionally Inserted on Chromosome Based on the chromosomal homologous recombination, the vector pDZTN-N0862 prepared in Example 5 was used to transform a L-lysine-producing strain, Corynebacterium glutamicum KCCM11016P. Afterwards, colonies were selectively screened therefrom by PCR (using primers of SEQ ID NOs: 12 and 13), and the resulting strain was named KCCM11016P::N0862-Tn. KCCM11016P::N0862-Tn and a control group were each cultured in the same manner as in Example 2, and then, the concentrations of L-lysine in the cultures were analyzed as shown below (see Table 3).

TABLE 3

| Strain number | | 1st Lysine concentration (g/L) | 1st Average (g/L) | 2nd Lysine concentration (g/L) | 2nd Average (g/L) | 3rd Lysine concentration (g/L) | 3rd Average (g/L) |
|---|---|---|---|---|---|---|---|
| KCCM11016P | 1 | 42.1 | 42.6 | 43.5 | 42.6 | 42.6 | 42.5 |
| | 2 | 42.5 | | 42.5 | | 43.1 | |
| | 3 | 43.1 | | 41.9 | | 41.9 | |

TABLE 3-continued

| Strain number | | 1st Lysine concentration (g/L) | 1st Average (g/L) | 2nd Lysine concentration (g/L) | 2nd Average (g/L) | 3rd Lysine concentration (g/L) | 3rd Average (g/L) |
|---|---|---|---|---|---|---|---|
| KCCM11016P::N0862-Tn | 1 | 45.6 | 46.2 | 45.4 | 45.2 | 46.1 | 45.7 |
| | 2 | 46.8 | | 45.2 | | 45.9 | |
| | 3 | 46.2 | | 45.1 | | 45.1 | |

As a result, it was confirmed that the lysine producibility of KCCM11016P::N0862-Tn, which was the strain having the NCgl0862 gene additionally inserted on chromosome, was increased by 8% compared to the parent strain, KCCM11016P.

EXAMPLE 7

Production of L-lysine using KCCM10770P-derived Microorganism Including NCgl0862 Additionally Inserted on Chromosome The vector pDZTN-N0862 prepared in Example 5 was used to transform *Corynebacterium glutamicum* KCCM10770P, which was a lysine-producing strain in which 7 types of genes involved in the L-lysine biosynthesis pathway were additionally added to the chromosome thereof. Afterwards, a strain in which the NCgl0862 gene was additionally inserted on chromosome was selected by PCR, and the resulting strain was named *Corynebacterium glutamicum* KCCM10770P::N0862-Tn. The strain was cultured in the same manner as in Example 2, and then, the concentrations of L-lysine in the culture were analyzed as shown below (Table 4).

TABLE 4

| Strain number | | 1st Lysine concentration (g/L) | 1st Average (g/L) | 2nd Lysine concentration (g/L) | 2nd Average (g/L) | 3rd Lysine concentration (g/L) | 3rd Average (g/L) |
|---|---|---|---|---|---|---|---|
| KCCM10770P | 1 | 45.8 | 46.3 | 45.9 | 46.5 | 45.9 | 45.9 |
| | 2 | 46.2 | | 46.8 | | 45.7 | |
| | 3 | 46.8 | | 46.7 | | 46.1 | |
| KCCM10770P::N0862-Tn | 1 | 48.1 | 48.6 | 48.6 | 48.7 | 48.5 | 48.6 |
| | 2 | 49.1 | | 47.5 | | 48.7 | |
| | 3 | 48.7 | | 49.9 | | 48.6 | |

As a result, it was confirmed that the lysine producibility was increased by 5% compared to the parent strain.

EXAMPLE 8

Production of L-lysine using CJ3P-derived Microorganism Including NCgl0862 Additionally Inserted on Chromosome To identify the effects in other strains belonging to *Corynebacterium glutamicum*, the vector pDZTN-N0862 prepared in Example 5 was used to transform *Corynebacterium glutamicum* CJ3P, which was a lysine-producing strain having 3 types of gene mutations associated with the improvements of L-lysine producibility. Afterwards, a strain in which the NCgl0862 gene was additionally inserted on chromosome were selected by PCR, and the resulting strain was named CJ3P::N0862-Tn. The strain was cultured in the same manner as in Example 2, and then, the concentrations of L-lysine recovered therefrom were analyzed as shown below (see Table 5).

TABLE 5

| Strain number | | 1st Lysine concentration (g/L) | 1st Average (g/L) | 2nd Lysine concentration (g/L) | 2nd Average (g/L) | 3rd Lysine concentration (g/L) | 3rd Average (g/L) |
|---|---|---|---|---|---|---|---|
| CJ3P | 1 | 8.0 | 8.0 | 7.9 | 8.0 | 8.1 | 8.1 |
| | 2 | 7.9 | | 8.1 | | 8.2 | |
| | 3 | 8.1 | | 8.0 | | 8.0 | |

TABLE 5-continued

| Strain number | | 1st Lysine concentration (g/L) | 1st Average (g/L) | 2nd Lysine concentration (g/L) | 2nd Average (g/L) | 3rd Lysine concentration (g/L) | 3rd Average (g/L) |
|---|---|---|---|---|---|---|---|
| CJ3P::N0862-Tn | 1 | 9.3 | 9.1 | 9.1 | 9.0 | 9.1 | 9.2 |
| | 2 | 9.1 | | 8.9 | | 8.9 | |
| | 3 | 8.9 | | 9.1 | | 9.5 | |

As a result, it was confirmed that the lysine producibility was increased by 12% compared to the parent strain.

EXAMPLE 9

Production of L-lysine using KCCM11347P-derived Microorganism Including NCgl0862 Inserted on Chromosome To identify the effects of other strains belonging to *Corynebacterium glutamicum*, the vector pDZTN-N0862 was introduced into a L-lysine producing strain, *Corynebacterium glutamicum* KCCM11347P (Korean Patent No. 1994-0001307) in the same way as Example 5, and the resulting strain was named KCCM11347P::N0862-Tn. The strain was cultured in the same manner as in Example 2, and then, the concentrations of L-lysine recovered therefrom were analyzed as shown below (see Table 6).

TABLE 6

| Strain number | | 1st Lysine concentration (g/L) | 1st Average (g/L) | 2nd Lysine concentration (g/L) | 2nd Average (g/L) | 3rd Lysine concentration (g/L) | 3rd Average (g/L) |
|---|---|---|---|---|---|---|---|
| KCCM11347P | 1 | 37.9 | 38.2 | 38.1 | 38.2 | 37.9 | 38.4 |
| | 2 | 38.7 | | 38.0 | | 39.1 | |
| | 3 | 38.1 | | 38.6 | | 38.2 | |
| KCCM11347P::N0862-Tn | 1 | 40.2 | 40.3 | 41.1 | 40.5 | 41.1 | 40.9 |
| | 2 | 39.9 | | 40.5 | | 40.1 | |
| | 3 | 39.8 | | 39.9 | | 41.5 | |

As a result, it was confirmed that the lysine producibility was increased by 6% compared to the parent strain.

Name of Depositary Institution: Korean Culture Center of Microorganisms (International)
Accession Number: KCCM11347P
Accession Date: 19911210

Name of Depositary Institution: Korean Culture Center of Microorganisms (International)
Accession Number: KCCM11430P
Accession Date: 20130612

The invention claimed is:

1. A microorganism belonging to the genus *Corynebacterium* producing L-lysine with improved expression of a polynucleotide encoding an amino acid sequence of SEQ ID NO: 1.

2. The microorganism of claim 1, wherein the improved expression is induced by an increase in copy number of genes, manipulation of an expression regulatory sequence, or combinations thereof.

3. The microorganism of claim 1, wherein the microorganism is *Corynebacterium glutamicum*.

4. A method of producing L-lysine, the method comprising:

culturing the microorganism of claim 1 in a medium; and recovering L-lysine from the microorganism or the medium.

* * * * *

SEQUENCE LISTING

<160> NUMBER OF SEQ ID NOS: 13

<210> SEQ ID NO 1
<211> LENGTH: 98
<212> TYPE: PRT
<213> ORGANISM: Corynebacterium glutamicum

<400> SEQUENCE: 1

Met Glu Ala Glu Ala Pro Val Glu Asp Leu Ser Ala Phe Ile Glu Gln
1               5                   10                  15

Glu Lys Ala Ser Phe Pro Ile Thr Trp Met Cys Arg Lys Leu Gly Val
            20                  25                  30

Ser Arg Ala Ser Tyr Tyr Arg Trp Ala Lys Pro Ala Gly Leu Thr Pro
        35                  40                  45

Thr Ala Ile Arg His Leu Glu Leu Arg Ala Glu Val Ala Gln Glu Phe
    50                  55                  60

Glu Lys Ser Asn Gln Met Ala Gly Arg Asp Gln Leu Thr Thr Leu Leu
65                  70                  75                  80

Asn Gln Arg Gly Val Lys Val Ser Thr Gly Thr Val Gly Ser Ile Met
                85                  90                  95

Asn Glu

<210> SEQ ID NO 2
<211> LENGTH: 297
<212> TYPE: DNA
<213> ORGANISM: Corynebacterium glutamicum

<400> SEQUENCE: 2
ttggaagccg aagcacctgt agaggatctc tcagcgttca tcgagcaaga gaaggcgtcg      60
tttcccatta catggatgtg cagaaagttg ggtgtgtcca gagcgtcgta ttaccggtgg     120
gccaagcctg cgggtctgac tccgacagcc ataaggcatt tagaactcag ggctgaggtt     180
gcccaggagt ttgaaaaaag caaccagatg gctggcaggg atcagctgac cacgttgctc     240
aaccagcgtg gtgtcaaagt ttctactggg actgtgggat caattatgaa cgaatga       297

<210> SEQ ID NO 3
<211> LENGTH: 24
<212> TYPE: DNA
<213> ORGANISM: Artificial Sequence
<220> FEATURE:
<223> OTHER INFORMATION: library_primer_F

<400> SEQUENCE: 3
tcagggtgta gcggttcggt ttat                                            24

<210> SEQ ID NO 4
<211> LENGTH: 24
<212> TYPE: DNA
<213> ORGANISM: Artificial Sequence
<220> FEATURE:
<223> OTHER INFORMATION: library_primer_R

<400> SEQUENCE: 4
ccgcgcgtaa tacgactcac tata                                            24

<210> SEQ ID NO 5
<211> LENGTH: 24
<212> TYPE: DNA
<213> ORGANISM: Artificial Sequence
<220> FEATURE:
<223> OTHER INFORMATION: 0862up_primer_F

<400> SEQUENCE: 5
gtgaattccg cccgtatggt gatt                                              24

<210> SEQ ID NO 6
<211> LENGTH: 23
<212> TYPE: DNA
<213> ORGANISM: Artificial Sequence
<220> FEATURE:
<223> OTHER INFORMATION: 0862up_primer_R

<400> SEQUENCE: 6
taggatccag aaggcgctgg ctt                                               23

<210> SEQ ID NO 7
<211> LENGTH: 32
<212> TYPE: DNA
<213> ORGANISM: Artificial Sequence
<220> FEATURE:
<223> OTHER INFORMATION: 0862dn_primer_F

<400> SEQUENCE: 7
agggatccta acatatggaa gccgaagcac ct                                     32

<210> SEQ ID NO 8
<211> LENGTH: 24
<212> TYPE: DNA
<213> ORGANISM: Artificial Sequence
<220> FEATURE:
<223> OTHER INFORMATION: 0862dn_primer_R

<400> SEQUENCE: 8
aggtcgactc attcgttcat aatt                                              24

<210> SEQ ID NO 9
<211> LENGTH: 28
<212> TYPE: DNA
<213> ORGANISM: Artificial Sequence
<220> FEATURE:
<223> OTHER INFORMATION: lysCP_primer_F

<400> SEQUENCE: 9
taggatccta gggagccatc ttttgggg                                          28

<210> SEQ ID NO 10
<211> LENGTH: 29
<212> TYPE: DNA
<213> ORGANISM: Artificial Sequence
<220> FEATURE:
<223> OTHER INFORMATION: lysCP_primer_R

<400> SEQUENCE: 10
taacatatgt gtgcaccttt cgatctacg                                         29

<210> SEQ ID NO 11
<211> LENGTH: 28
<212> TYPE: DNA
<213> ORGANISM: Artificial Sequence
<220> FEATURE:
<223> OTHER INFORMATION: lysCP1_primer_F

<400> SEQUENCE: 11
taactagtta gggagccatc ttttgggg                                          28

<210> SEQ ID NO 12

```
<211> LENGTH: 24
<212> TYPE: DNA
<213> ORGANISM: Artificial Sequence
<220> FEATURE:
<223> OTHER INFORMATION: pDZTN_N0862_primer_F

<400> SEQUENCE: 12
taactagtat gctcggtccg ggca                                        24

<210> SEQ ID NO 13
<211> LENGTH: 20
<212> TYPE: DNA
<213> ORGANISM: Artificial Sequence
<220> FEATURE:
<223> OTHER INFORMATION: pDZTN_N0862_primer_R

<400> SEQUENCE: 13
gcaggcggtg agcttgtcac                                             20
```